(12) United States Patent
Jeong

(10) Patent No.: US 12,082,958 B2
(45) Date of Patent: Sep. 10, 2024

(54) SYSTEM AND METHOD FOR DETECTING INTERNAL LOAD BY USING X-RAY IMAGE OF CONTAINER

(71) Applicant: ELECTRONICS AND TELECOMMUNICATIONS RESEARCH INSTITUTE, Daejeon (KR)

(72) Inventor: Ji Wook Jeong, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 267 days.

(21) Appl. No.: 17/868,554

(22) Filed: Jul. 19, 2022

(65) Prior Publication Data
US 2023/0210481 A1   Jul. 6, 2023

(30) Foreign Application Priority Data
Jan. 3, 2022   (KR) .................. 10-2022-0000496

(51) Int. Cl.
*A61B 6/42* (2024.01)
*A61B 6/58* (2024.01)

(52) U.S. Cl.
CPC ............ *A61B 6/4291* (2013.01); *A61B 6/583* (2013.01); *A61B 6/584* (2013.01)

(58) Field of Classification Search
CPC ....... A61B 6/4291; A61B 6/583; A61B 6/584; G01V 5/20; G06T 7/11; G06T 5/70; G06T 7/001; G06T 7/194; G06T 11/005; G06T 2207/10116; G06T 2207/20224
See application file for complete search history.

(56) References Cited

U.S. PATENT DOCUMENTS

| | | |
|---|---|---|
| 8,538,118 B2 | 9/2013 | Baba |
| 2011/0118131 A1 | 5/2011 | Takeuchi |
| 2015/0235105 A1 | 8/2015 | Han et al. |
| 2017/0242148 A1* | 8/2017 | Yu ........................... G01V 5/22 |

FOREIGN PATENT DOCUMENTS

| | | |
|---|---|---|
| CN | 103824281 A | 5/2014 |
| CN | 104077743 A | 10/2014 |
| KR | 10-2269741 B1 | 6/2021 |

* cited by examiner

*Primary Examiner* — Courtney D Thomas
(74) *Attorney, Agent, or Firm* — Rabin & Berdo, P.C.

(57) ABSTRACT

Provided is a system for detecting an internal load by using an X-ray image of a container. The system includes an X-ray imaging unit and configured to image a target with X-rays, a database that stores an X-ray reference image obtained by imaging a target having an empty interior according to X-ray imaging information including an X-ray imaging condition, a condition detection unit that acquires X-ray imaging information when the target is imaged, a comparison image selection unit that selects an X-ray reference image from the database, a matching unit that matches a difference between the X-ray image of the target and the selected X-ray reference image, and an internal load detection unit that obtains a difference image from the X-ray image and the X-ray reference image, and detects an internal loading image having no background of the X-ray image of the target through the obtained difference image.

20 Claims, 8 Drawing Sheets

INPUT IMAGED CONTAINER IMAGE

IMAGING CONDITION A    IMAGING CONDITION B

EXAMPLE OF CONTAINER IMAGING CONDITION LEARNING AND INFERRING PROCESS

SELECT CORRESPONDING IMAGING CONDITION AND BACKGROUND IMAGE IN IMAGE DATA SET ACCORDING TO CONTAINER IMAGING CONDITION

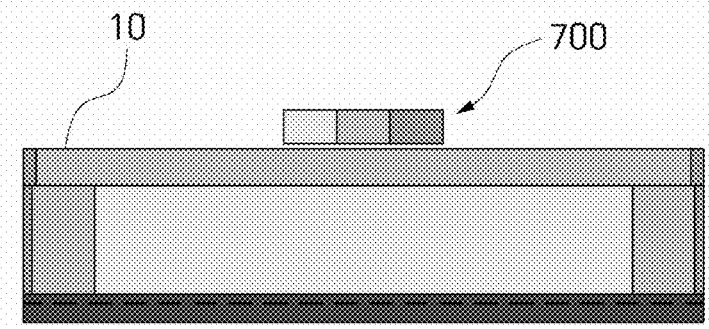
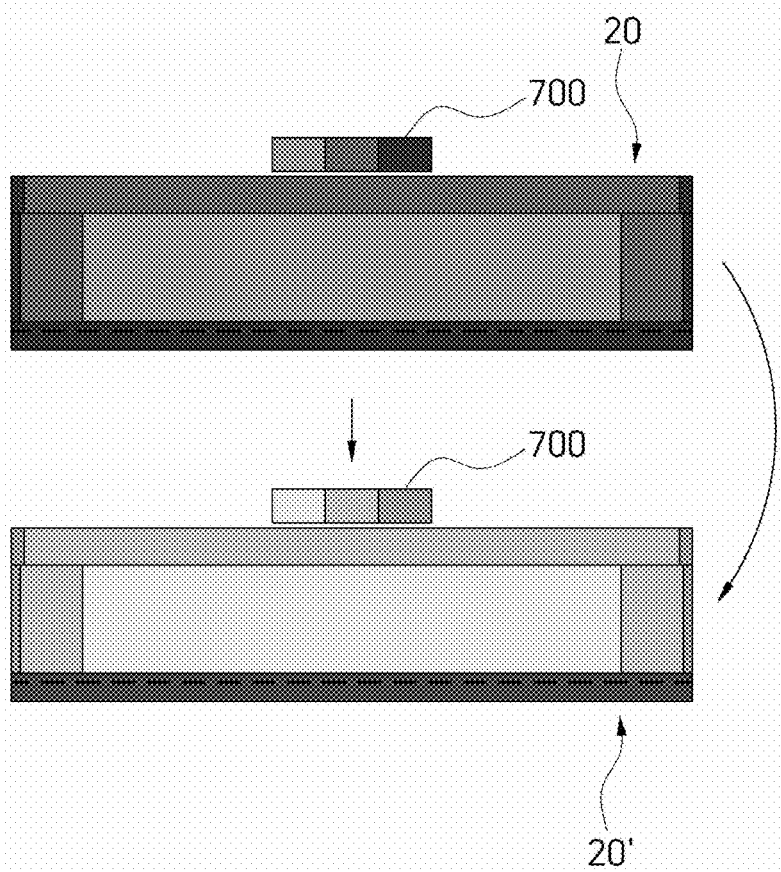

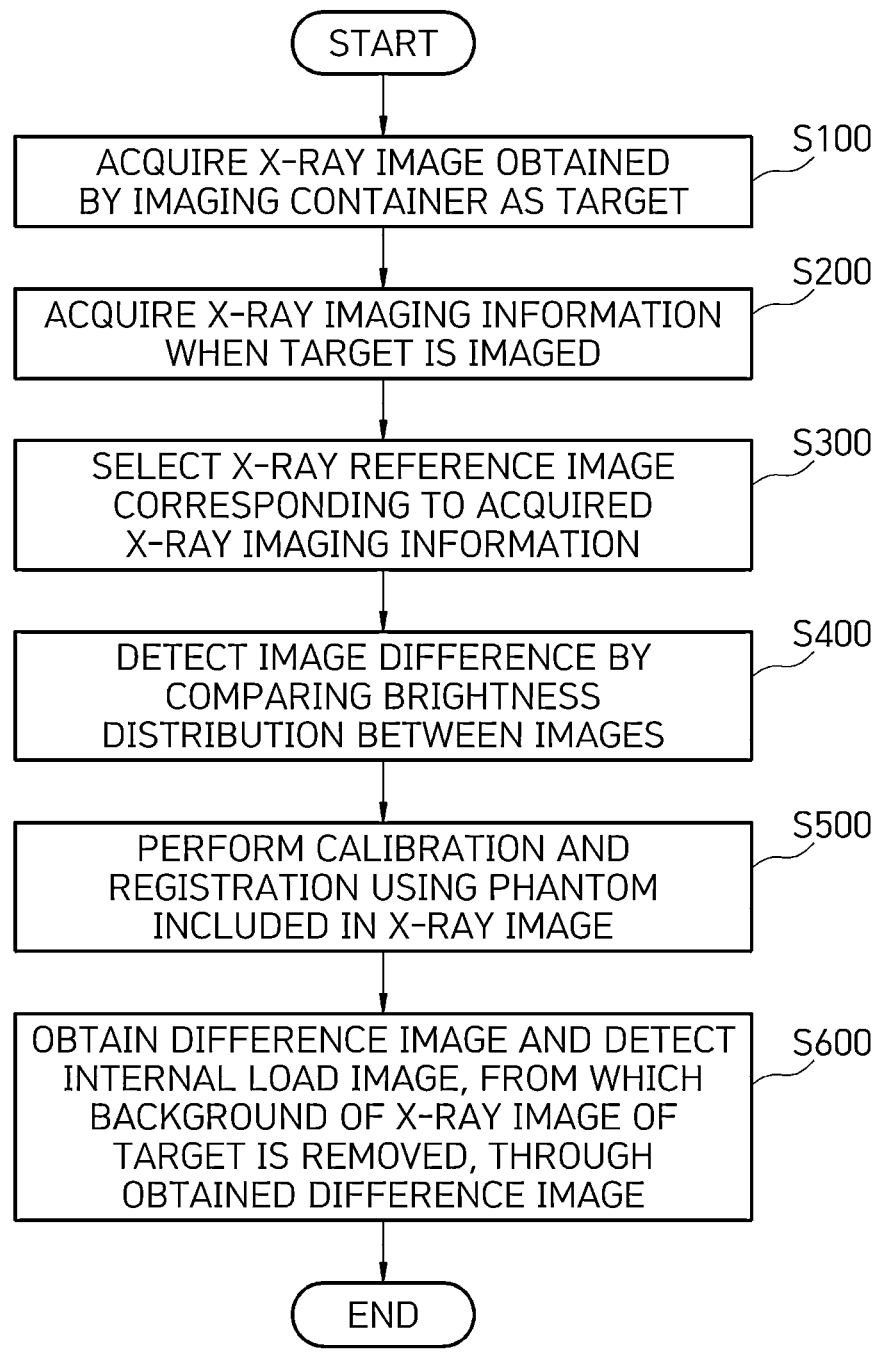

TARGET INCLUDING INTERNAL LOAD

EMPTY TARGET

REGISTERED TARGET INCLUDING INTERNAL LOAD

SYSTEM AND METHOD FOR DETECTING INTERNAL LOAD BY USING X-RAY IMAGE OF CONTAINER

CROSS-REFERENCE TO RELATED APPLICATIONS

This application claims the benefit under 35 USC § 119(a) of Korean Patent Application No. 10-2022-0000496, filed on Jan. 3, 2022 in the Korean Intellectual Property Office, the entire disclosure of which is incorporated herein by reference for all purposes.

BACKGROUND

1. Technical Field

The present disclosure relates to a system for detecting an internal load by using an X-ray image of a container, and more particularly, to a system for detecting an internal load using an X-ray image of a container, which detects an object existing in the container by using a container image taken through X-ray.

2. Related Art

With the development of artificial intelligence technology, artificial intelligence is being used in various fields.

The prediction performance of a neural network used in artificial intelligence depends on a learning method, and various learning methods may be applied depending on an application field. For example, in the field of detecting an internal load, a supervised learning method may be used to annotate in advance information on a detection target in learning data and repeatedly train a neural network to output the annotated result.

Recently, many methods have been developed to detect various internal loads existing in an image and determine the type of the internal loads by using a neural network model trained through such a supervised learning method.

However, since these methods mainly determine an internal load on the basis of a specific shape and color distribution in a visible ray region, it may be difficult to directly apply the methods to a special image such as an X-ray image.

Usually, in the case of internal loads stored in a container, since the internal loads are imaged in a situation where the internal loads are distributed in multiple layers in the container. Therefore, in a baggage X-ray image and a container X-ray transmission image, not only various internal loads themselves are overlappingly imaged, but also a background image not to be detected, that is, transmission images of the internal loads and the container itself, are also overlappingly imaged, which may reduce detection performance.

SUMMARY

Various embodiments are directed to a system for detecting an internal load by using an X-ray image of a container, which detects an internal load of a container through a method for removing a background including a case such as a container constituting a background not to be detected in a container X-ray image and a baggage X-ray image.

Also, various embodiments are specifically directed to a system for detecting an internal load by using an X-ray image of a container, which generates a pre-processing image that is easier to detect an internal load by removing a loading container, that is, a container background, which overlaps in common in a container transmission image to be detected.

However, the problems to be solved by the present disclosure are not limited to the above-described problems, and other problems may be present.

In order to solve the above-described problems, a system for detecting an internal load by using an X-ray image of a container in accordance with an embodiment of the present disclosure may include: an X-ray imaging unit including a source and a director and configured to image a target with X-rays; a database configured to store an X-ray reference image obtained by imaging a target having an empty interior according to X-ray imaging information including an X-ray imaging condition; a condition detection unit configured to acquire X-ray imaging information when the target is imaged through the X-ray imaging unit; a comparison image selection unit configured to select an X-ray reference image corresponding to the acquired X-ray imaging information from the database; a matching unit configured to match a difference between the X-ray image of the target and the selected X-ray reference image; and an internal load detection unit configured to obtain a difference image from the X-ray image of the matched target and the X-ray reference image, and to detect an internal loading image having no background of the X-ray image of the target through the obtained difference image.

The X-ray imaging information may include at least one condition of a standard of an imaging target for a target having an empty interior, a relative geometric condition between the imaging target and the source of the X-rays, a relative geometric condition between the imaging target and the detector, and an X-ray frequency.

The database may store an X-ray reference image according to the standard of the imaging target for the target having an empty interior, the relative geometric condition between the imaging target and the source of the X-rays, the relative geometric condition between the imaging target and the detector, and the X-ray frequency.

The database may store at least one X-ray reference image of an X-ray image imaged by a combination of a stationary source and a moving line detector and an X-ray image imaged by a combination of a moving source and the moving line detector.

In the database, an X-ray reference image, which is imaged using one condition of a distance between the target and the X-ray imaging unit, a height from the ground, an inclination of the target, an X-ray wavelength, a type of the detector of spatial resolution, a calibration phantom, and a type of a registration phantom, may be set as a data set for storage.

In the database, a computer graphics simulation image can be generated using the above imaging condition and target type as parameters and stored.

The internal load detection unit may transmit information on a location and a type of the detected internal load to a display screen.

The system may further include a noise removal algorithm for removing grid noise generated between the source and the director during various X-ray imaging.

Furthermore, the system may further include a calibration phantom that is imaged with X-rays together with the target having an internal accommodating space in order to perform calibration of an image taken with X-rays and a registration phantom that is imaged with X-rays together with the target having an internal accommodating space in order to perform registration of the image taken with X-rays, and the matching unit may perform the calibration and the registration by using a predetermined phantom imaged together with the target.

Preferably, in the calibration phantom, a sample including a plurality of materials perpendicular to an axis of the source and the detector, which do not overlap each other, and having the same thickness may be arranged on a plane parallel to the axis.

Preferably, the registration phantom may be attached at the outermost vertex position of the target so as not to overlap the shadow of the target.

The sample may be any one of steel and non-ferrous metal.

The correction unit may calibrate the X-ray image of the target loaded with the internal load and the X-ray reference image having the same geometric condition and same wavelength corresponding to the X-ray image.

The correction unit may register the X-ray image of the target loaded with the internal load and the X-ray reference image having the same geometric condition and same wavelength corresponding to the X-ray image.

The correction unit may detect a major key point of a two-dimensional projection container skeleton using a machine learning method including deep learning and a characteristic analysis method, detect a geometric condition that matches a distribution of a corresponding key point through one-to-one correspondence, and select an image imaged with a wavelength that matches or is similar to an X-ray wavelength of the X-ray imaging unit.

The correction unit may detect a phantom for calibration installed so as not to overlap a region of the target loaded with an internal load, fix a color tone conversion formula through linear or non-linear regression so that two regions have statistically the same brightness distribution, and convert an X-ray image by applying the color tone conversion formula to the X-ray image of the entire target loaded with the internal load.

The correction unit may detect a phantom for registration installed so as not to overlap the region of the target loaded with an internal load, match the phantom pair installed in the same relative position as a region of an empty target, fix a spatial conversion formula between matching phantom positions, and convert an X-ray image by applying the spatial conversion formula to the X-ray image of the entire target loaded with the internal load.

The correction unit may perform a comparison using one of a method for comparing a specific geometric condition of the X-ray reference image with geometric conditions corresponding to key points in a one-to-one manner inferred from the X-ray image of the target loaded with the internal load, a method for directly comparing combinations of key points respectively inferred from the X-ray reference image and the X-ray image of the target loaded with the internal load, a method for comparing a specific geometric condition of the X-ray image of the target loaded with the internal load with geometric conditions corresponding to key points in a one-to-one manner inferred from the X-ray reference image, and a method for directly comparing geometric conditions of the X-ray reference image with geometric conditions of the X-ray image of the target loaded with the internal load.

When geometric conditions, wavelengths, and spatial resolutions of the X-ray image of the target loaded with the internal load and the X-ray reference image do not exactly match, the correction unit may infer a new X-ray reference image by a linear or non-linear regression method from X-ray reference images of two or more adjacent conditions according to imaging conditions of the X-ray image of the target loaded with the internal load, and select or generate an optimal condition.

Preferably, a difference image between the two X-ray images may be obtained by obtaining a log image of the X-ray image of the imaged target, obtaining a difference between the log image of the X-ray image of the target and a log image of the X-ray reference image, and applying an exponential function from the difference.

When an internal load is detected in an X-ray image of an existing container including no calibration phantom, the correction unit may compare a distribution of shades in a region of a target where no internal load is distributed, for example, a skeletal part constituting a ceiling, a floor, and side walls.

When an internal load is detected in an X-ray image of an existing container including no registration phantom, the correction unit may compare a distribution of shades in a region of a target where no internal load is distributed, for example, a skeletal part constituting a ceiling, a floor, and side walls.

The system may further include a learning unit configured to train using a location and a type of the detected internal load.

A method for detecting an internal load by using an X-ray image of a container may include: a step of, by an X-ray imaging unit including a source and a detector, imaging a target with X-rays; a step of, by a condition detection unit, acquiring X-ray imaging information when the target is imaged through the X-ray imaging unit; a step of, by a comparison image selection unit, selecting an X-ray reference image corresponding to the acquired X-ray imaging information from a database; a step of detecting an image difference by comparing a brightness distribution between an X-ray image including a phantom region imaged together with the target loaded with an internal load and the selected X-ray reference image; a step of, when the difference in the brightness distribution between the X-ray image and the X-ray reference image is detected, performing calibration and registration using a phantom included in the X-ray image; a step of, by a matching unit, matches the difference between the X-ray image of the target and the selected X-ray reference image; and a step of, by a load detection unit, obtaining a difference image from the X-ray image of the matched target and the X-ray reference image, and detecting an internal load image, from which a background of the X-ray image of the target is removed, through the obtained difference image.

Preferably, the database may include an X-ray reference image according to a standard of an imaging target for a target having an empty interior, a relative geometric condition between the imaging target and the source of the X-rays, a relative geometric condition between the imaging target and the detector, and an X-ray wavelength.

In further another embodiment of the present disclosure, in a planar X-ray non-destructive inspection, after acquiring a two-dimensional image of a target to be inspected for actual defects compared to an X-ray two-dimensional image database of a ready-made structure for which defects are to be found, defects in a difference image may be detected by applying the internal load detection algorithm.

In yet another embodiment of the present disclosure, in an 3-dimensional CT non-destructive inspection, after acquiring a 3-dimensional image of a target to be inspected for actual defects compared to an X-ray 3D image database of a 3D ready-made structure for which defects are to be found, defects in a difference image may be detected by applying the internal load detection algorithm.

In accordance with another embodiment of the present disclosure, there is an effect capable of detecting an internal load accommodated in a container having no phantom region.

BRIEF DESCRIPTION OF THE DRAWINGS

FIGS. 6A and 6B are a reference diagram for explaining a correction process using a calibration phantom in an embodiment of the present disclosure.

FIG. 7 is a flowchart for explaining a method for detecting an internal load using an X-ray image of a container according to an embodiment of the present disclosure.

DETAILED DESCRIPTION

The advantages and characteristics of the present disclosure and a method for achieving the advantages and characteristics will be clearly understood through embodiments to be described in detail together with the accompanying drawings. However, the present disclosure is not limited to the following embodiments, but may be implemented in various shapes different from each other, and the present embodiments are provided to bring the disclosure of the present disclosure to perfection and assist those skilled in the art to completely understand the scope of the present disclosure. Therefore, the present disclosure is defined only by the scope of the appended claims. Terms used in the present specification are used for describing embodiments, not limiting the present disclosure. The terms of a singular form in the present specification may include plural forms unless specifically mentioned. The meaning of 'comprise' and 'comprising' used in the specification does not exclude the presence or addition of one or more other components in addition to the mentioned components.

Figure 1:
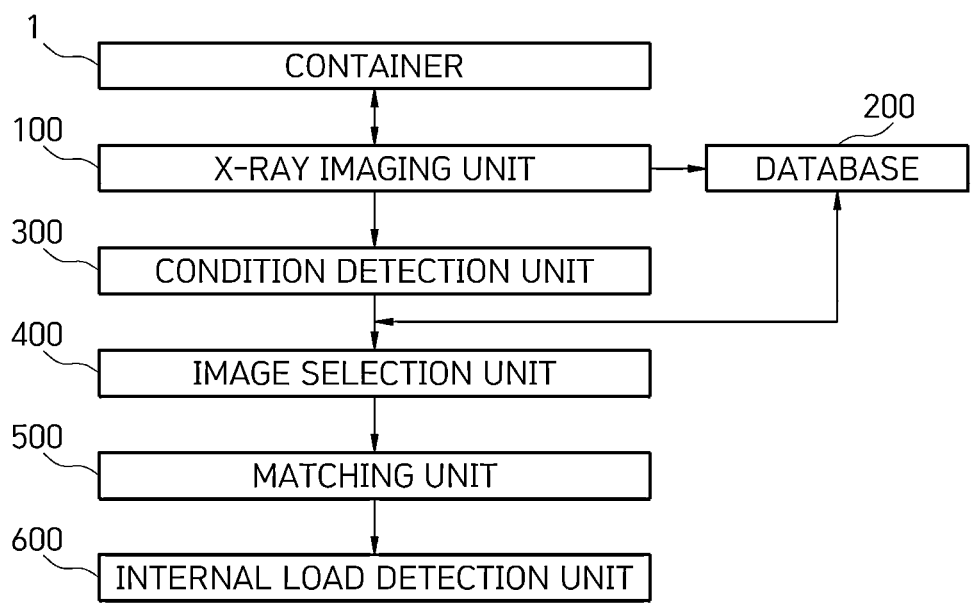
FIG. 1 is a configuration block diagram for explaining a system for detecting an internal load by using an X-ray image of a container in accordance with an embodiment of the present disclosure.

FIG. 1 is a configuration block diagram for explaining a system for detecting an internal load by using an X-ray image of a container in accordance with an embodiment of the present disclosure.

As illustrated in FIG. 1, the system for detecting an internal load by using an X-ray image of a container in accordance with an embodiment of the present disclosure includes an X-ray imaging unit 100, a database 200, a condition detection unit 300, an image selection unit 400, a matching unit 500, and an internal load detection unit 600.

Figure 2:
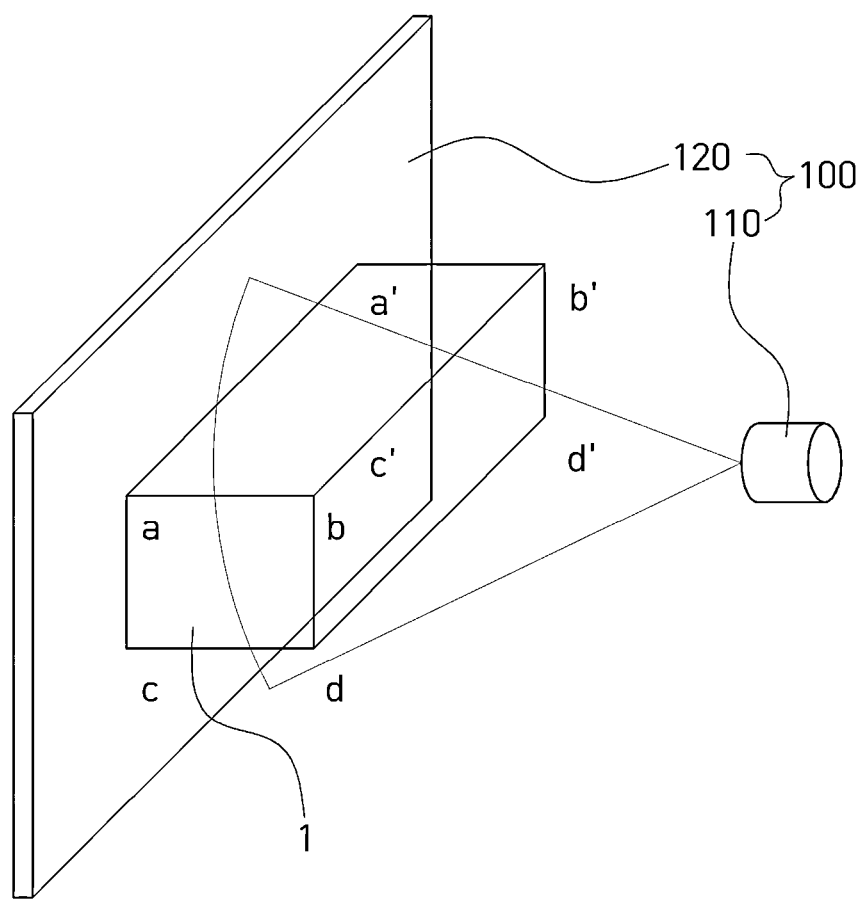
FIG. 2 is a reference diagram for explaining an example of imaging a container through an X-ray imaging unit of FIG. 1.
Figure 3:
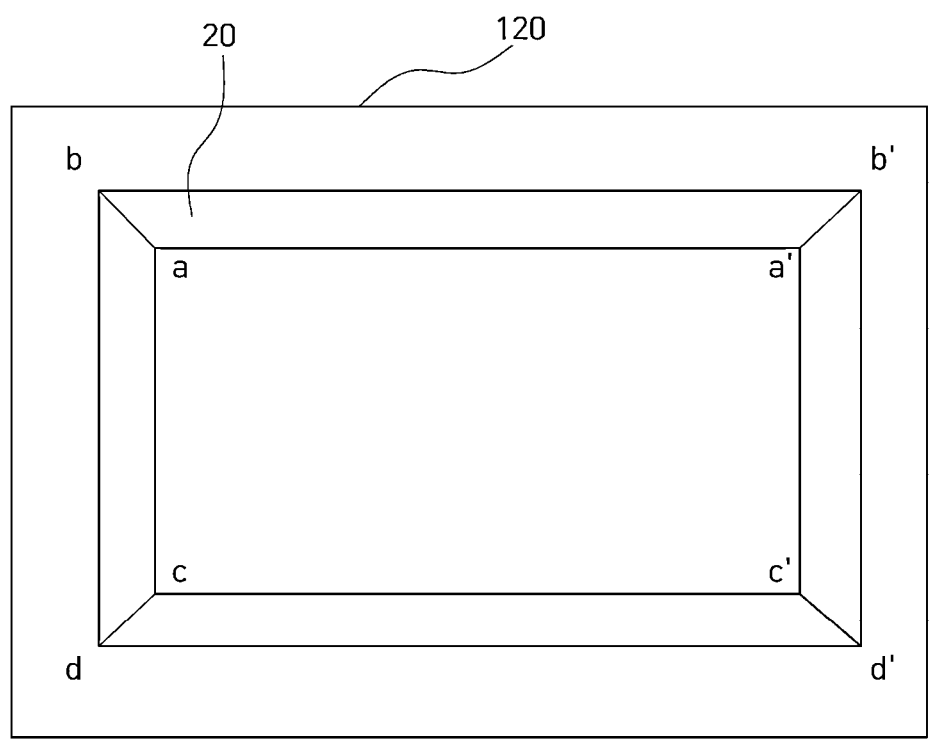
FIG. 3 is a diagram for explaining an example of an X-ray image or an X-ray reference image taken through an X-ray imaging unit of FIG. 2.

The X-ray imaging unit 100 is for imaging a container 1 as a target with X-rays, and as illustrated in FIG. 2, includes a source 110 for outputting X-rays and a director 120 provided on the rear side of the container 1 to detect the X-rays output from the source 110 and convert the X-rays into an image. The container 1 is imaged through the X-ray imaging unit 100 as illustrated in FIG. 2, resulting in a container image 20 of the container 1 as illustrated in FIG. 3, the container image 20 having a rectangular surface having vertices (a, c, a', and c') on the front side of the container and a rectangular surface having vertices (b, d, b', and d') on the rear side of the container, the rear rectangular surface being larger than the front rectangular surface.

The database 200 stores an X-ray reference image 10 according to the standard of an imaging target for the container 1, which is a target with an empty interior, a relative geometric condition between the imaging target and the X-ray source 110, and a relative geometric condition between the container to be imaged and the detector 12. Furthermore, in the database 200, X-ray image data of the container is constructed for each reference image 10 imaged by a combination of the stationary source 110—the moving line detector 120 or each X-ray image imaged by a combination of the moving source 110 and the moving line detector 120.

Furthermore, the database 200 stores an X-ray image imaged through one condition of a distance between the container and the X-ray imaging unit 100, a height from the ground, an inclination of the container, an X-ray wavelength, the type of the detector 120 of spatial resolution, a calibration phantom 700, and the type of a registration phantom.

Figure 4A:
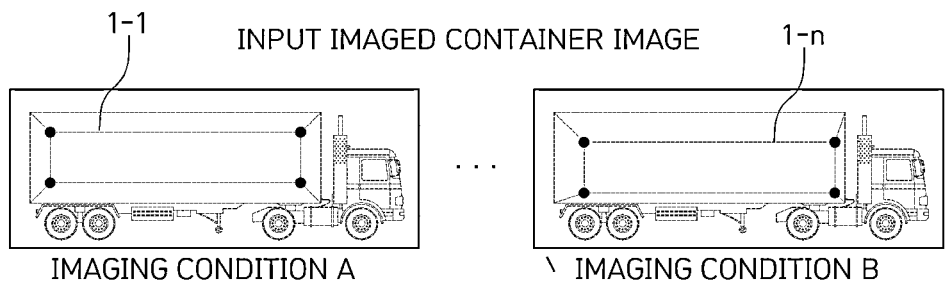
FIGS. 4A, 4B and 4C are a reference diagram for explaining an example of selecting an imaging condition by an image selection unit of FIG. 1.
Figure 4B:
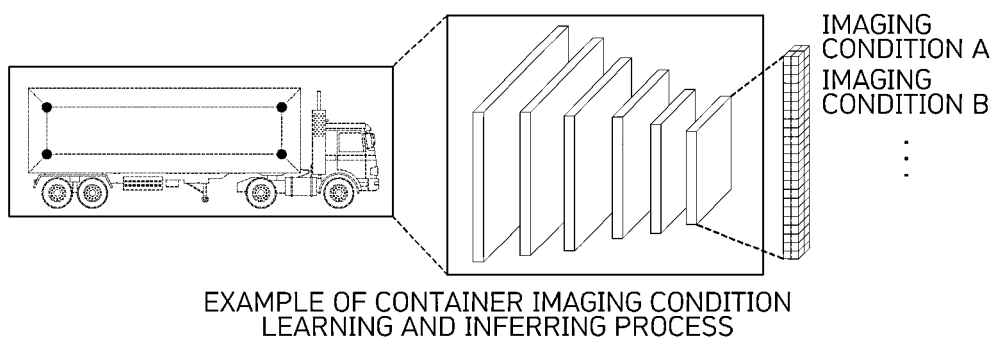
Figure 4C:
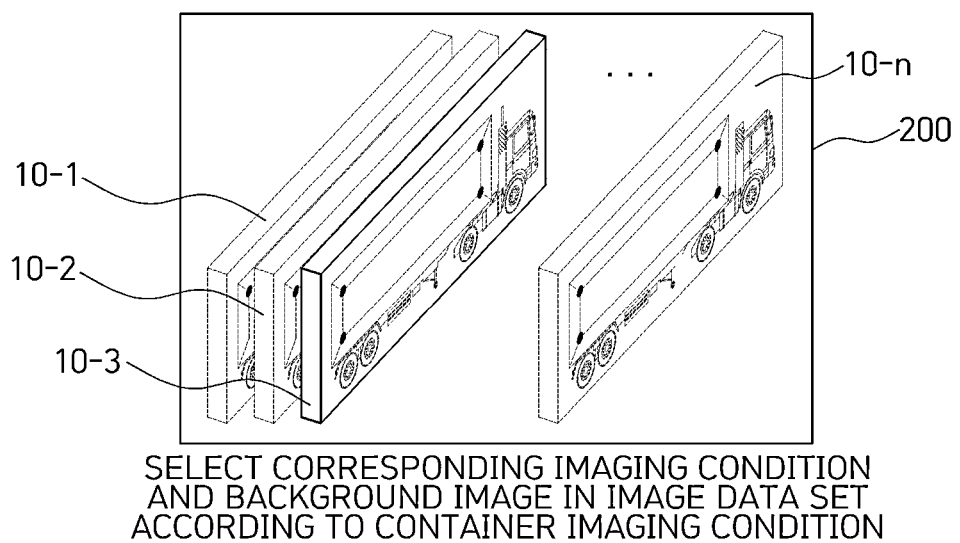

The condition detection unit 300 acquires the X-ray imaging information when a target is imaged through the X-ray imaging unit 100. The X-ray imaging information includes the standard of the imaging target, the relative geometric condition between the imaging target and the X-ray source 110, and the relative geometric condition between the imaging target and the detector 12 using an analogy technique such as machine learning, as illustrated in FIGS. 4A, 4B and 4C. The condition detection unit 300 of the present disclosure may include a noise removal algorithm for removing noise generated during various X-ray imaging, such as grid noise between the source 110 and the detector 120 (for example, in order to remove horizontal line noise appearing during imaging with a line detector, vertical Fourier transform in empty space cropped image or removal of pixel values below a threshold using histogram analysis may be used).

The X-ray imaging condition includes at least one of the standard of the container 1, a distance between the container to be imaged and the X-ray imaging unit, and a relative geometric condition between the container to be imaged and the detector 120.

The image selection unit 400 selects the container X-ray reference image 10 corresponding to an X-ray imaging condition from the database 200 when the target is imaged with X-rays.

The matching unit 500 matches the difference between the X-ray image 20 of the container imaged together with the container 1 and the container X-ray reference image 10 selected from the database 200. As an example, when the coordinates of an object (container) of the X-ray image 20 taken with X-rays and the coordinates of the object (container) of the X-ray reference image 10 stored in the database 200 are relatively different, the matching unit 500 corrects the object coordinates of the imaged X-ray image 20 to be identical to the selected X-ray reference image 10.

In the present embodiment, since the container as a target is standardized as a standard (20 feets or 40 feets), the object coordinates of the X-ray image 20 may be compared and matched with the coordinates of the object (container) of the X-ray reference image 10 on the basis of on the coordinates of one side of the container.

The internal load detection unit 600 obtains a difference image from the X-ray image 20 of the matched container and X-ray reference image 10, and removes the background of the container X-ray image 20 using the obtained difference image to detect an image of an internal load (dangerous goods). That is, due to X-ray characteristics of imaging the distribution of objects only through transmission, since a difference image between two images is not defined as the difference in simple pixel values, the internal load detection unit 600 preferably obtains log images of the imaged X-ray image, obtains a difference between the two log images, and applies an exponential function from the difference to obtain a difference image.

In the X-ray image 20 obtained by imaging the container having an internal load therein, the X-ray image 20 is expressed in which an object value of the internal load and an object value of the external container itself are in an exponential state.

Figure 5:
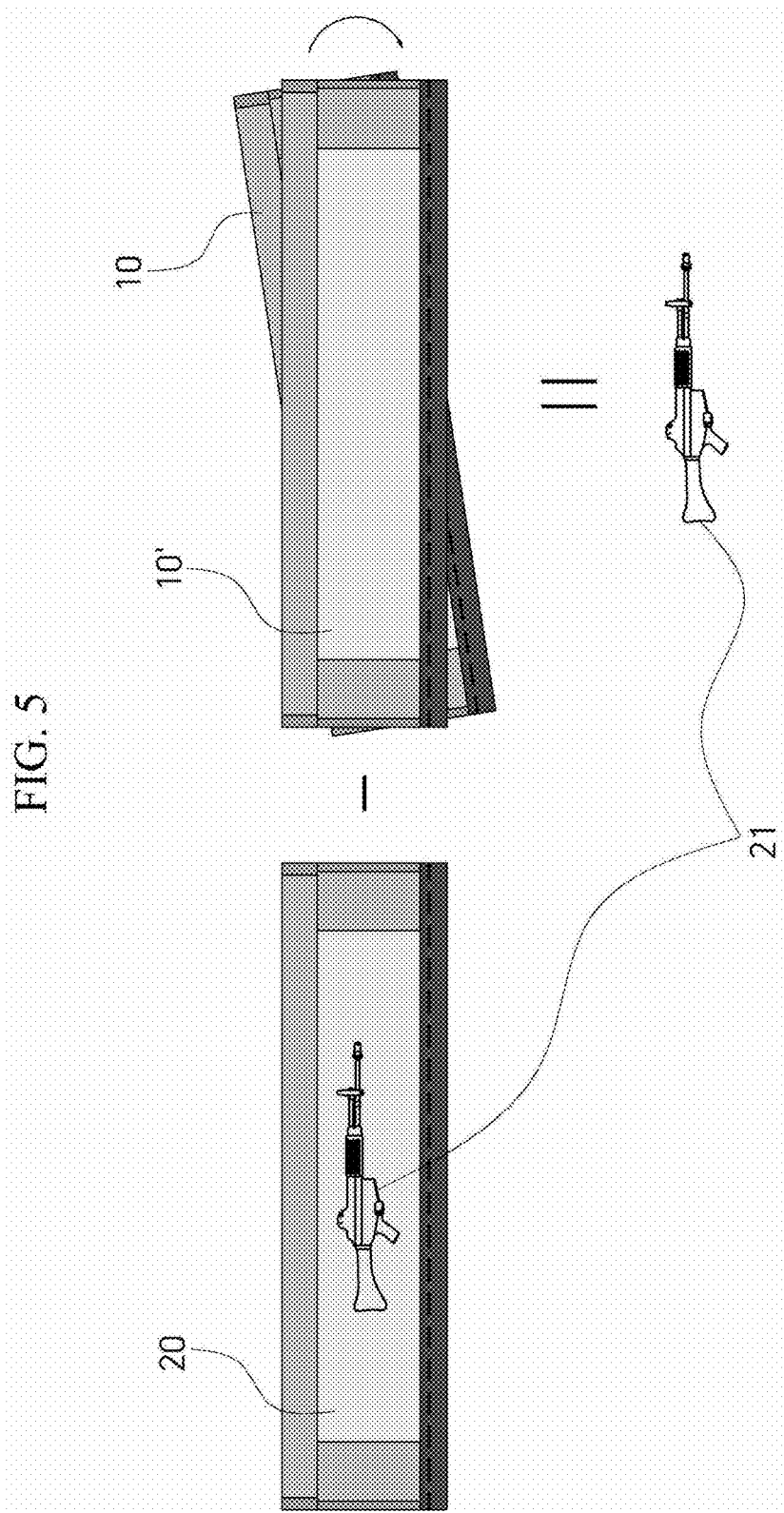
FIG. 5 is a reference diagram for explaining an operation of an internal load detection unit of FIG. 1.

In such a case, since the object value of the container itself has already been stored in the database 200, when the X-ray reference image 10 is subtracted from the X-ray image 20 of the imaged container, the internal load in the container may be detected as illustrated in FIG. 5.

Then, the internal load detection unit 600 transmits, to a display screen, a remote detection image in which detection information such as the location, type, and the like of dangerous goods is displayed on an imaged original X-ray image, an X-ray image with a removed background, and the like.

In accordance with an embodiment of the present disclosure, there is an effect capable of easily detecting an internal load mounted inside a container imaged under various conditions.

Furthermore, in accordance with an embodiment of the present disclosure, there is an effect that a container having an empty interior is imaged in advance under various conditions and stored in a database, an imaging condition of imaging the container loaded with an internal load is detected using an artificial intelligence technique and various learning methods, and the X-ray reference image 10 corresponding to the imaging condition is selected from the database, so that it is possible to easily detect the internal load inside the container from the X-ray image 20 imaged more easily.

Furthermore, in accordance with an embodiment of the present disclosure, there is an effect capable of improving detection performance by effectively removing pixels in a background region other than the internal load.

Another embodiment of the present disclosure further includes a calibration phantom 700 that is imaged together with a container having an accommodating space therein in order to perform calibration of an image taken with X-rays.

As illustrated in FIG. 6, in such a calibration phantom 700, a sample including a plurality of materials perpendicular to an axis of the source 110 and the detector 120, which do not overlap each other, and having the same thickness is preferably arranged on a plane parallel to the axis.

When the X-ray wavelength of the X-ray imaging unit 100 varies, such a calibration phantom 700 is used to correct the difference.

The material of the calibration phantom 700 is any one of steel and non-ferrous metal. In an embodiment of the present disclosure, the material of the calibration phantom is described as steel or non-ferrous metal, but is not limited thereto and may include various materials reflecting various attenuation characteristics. The phantom is installed so as not to overlap the container region.

A correction unit 800 selects the X-ray image 20 of the container loaded with the internal load as illustrated in FIG. 6A and the X-ray reference image 10 of a container having an empty interior, which has the same geometric condition and same wavelength as illustrated in FIG. 6B, from the database 200, and calibrates the X-ray image 20 of the container loaded with the internal load.

The image selection unit 400 detects major key points of a two-dimensional projection container skeleton by using a machine learning method including deep learning and other classical characteristic analysis methods. The key points mean eight vertices of the container.

Furthermore, the image selection unit 400 detects a geometric condition that matches the distribution of a corresponding key point through one-to-one correspondence.

Then, the image selection unit 400 detects an image imaged with a wavelength that matches or is similar to the X-ray wavelength of the X-ray imaging unit 100.

Furthermore, the image selection unit 400 automatically or manually checks the phantom for calibration that is installed so as not to overlap the container region when acquiring the X-ray image 20 of the container loaded with the internal load and is imaged at the same time.

Then, the image selection unit 400 may fix a color tone conversion formula through linear or non-linear regression so that the two regions have statistically the same distribution of brightness (for example, simply, a representative value is extracted from a plurality of sample regions in which the magnitude of a color tone value is determined, a linear or non-linear regression formula coefficient is obtained from a representative value distribution curve or a broken line, and a conversion coefficient for each color tone band is determined), and convert the X-ray image by applying this formula to the X-ray image 20 of the entire container loaded with the internal load.

The image selection unit 400 may compare geometric conditions between the X-ray image 20 of the container loaded with the internal load and the X-ray reference image 10 of the empty container for selection.

The image selection unit 400 may use one of a method for comparing a specific geometric condition of the X-ray reference image 10 of the empty container with geometric conditions corresponding to key points in a one-to-one manner inferred from the X-ray image 20 of the container loaded with the internal load, a method for directly comparing combinations of key points inferred from the X-ray reference image 10 of the empty container and the X-ray image 20 of the container loaded with the internal load, a method for comparing a specific geometric condition of the X-ray image 20 of the container loaded with the internal load with geometric conditions corresponding to key points in a one-to-one manner inferred from the X-ray reference image 10 of the empty container, and a method for directly comparing geometric conditions of the X-ray reference image 10 of the empty container with geometric conditions of the X-ray image 20 of the container loaded with the internal load.

That is, the image selection unit 400 may select one of the above types according to conditions of the border search site and construction conditions of the database 200.

When the geometric conditions, wavelengths, and spatial resolutions of the X-ray image 20 of the container loaded with the internal load and the X-ray reference image 10 of the empty container do not exactly match, the image selection unit 400 in accordance with an embodiment of the present disclosure may infer, select, or generate an X-ray reference image 10 of a new empty container by a linear or non-linear regression method from X-ray images of two or more adjacent conditions according to the conditions of the X-ray image 20 of the container loaded with the internal load.

Furthermore, according to the present disclosure, in the case of a system in which X-ray images of a plurality of containers are acquired by a pair of the source 110 and the detector 120 installed at a plurality of angles, a container reference image acquired under the condition of the pair of the source 110 and the detector 120 installed at the plurality of angles may be constructed in the database 200. In such a case, a plurality of phantoms need to be installed not to overlap container regions under respective imaging conditions when imaging a container loaded with an internal load and an empty container.

Furthermore, when an internal load is detected in an X-ray image of an existing container including no calibration phantom, the correction unit of the present disclosure compares the distribution of shades in a region of the container where no internal load is normally imaged, for example, a skeletal part constituting a ceiling, a floor, and side walls. In accordance with another embodiment of the present disclosure, there is an effect capable of detecting an internal load accommodated in a container including no phantom region.

For example, a linear or non-linear regression method may be used to define a formula (for example, simply, in the case of a container top plate region occurring due to imaging of the container top plate in a square shape, since there is an imaging angle at which there is generally no internal load, both an empty target and a target including an internal load need to overlap a steel plate within the angle. By using this, a representative value for each color tone may be extracted from a plurality of bands when imaging the top plate of the empty target and may be compared with a representative value for each color tone of the target including an internal load in the same manner, and a conversion coefficient for similar conversion between the representative values may be inferred) by comparing and similarly matching the distribution of shades of the skeleton part of a steel container projected on empty regions such as a ceiling and a floor of a container, X-ray images may be inferred to configure a corrected container X-ray image, and a difference image may be obtained from the corrected container X-ray image.

The present disclosure may include machine learning such as deep learning or other algorithms for, in order to transmit detection information such as the location and type of dangerous goods in an original image, a removal image and the like to a remote detection display screen, applying the machine learning or the other algorithms to a removal image provided immediately before transmission and determining the location and type of dangerous goods to be detected.

The present disclosure may detect and display all goods and types with specifiable image characteristics even though they are not dangerous goods.

Hereinafter, a method for detecting an internal load by using an X-ray image of a container in accordance with an embodiment of the present disclosure will be described with reference to FIG. 7.

First, the X-ray imaging unit 100 including the source 110 and the detector 120 acquires an X-ray image 20 obtained by imaging a container, which is a target, with X-rays (S100).

Then, the condition detection unit 300 acquires X-ray imaging information when the target is imaged through the X-ray imaging unit 100 (S200).

The comparison image selection unit 400 selects an X-ray reference image 10 corresponding to the acquired X-ray imaging information from the database 200 (S300). The database 200 stores an X-ray reference image 10 according to the standard of an imaging target for a target with an empty interior, a relative geometric condition between the imaging target and the X-ray source 110, and a relative geometric condition between the imaging target and the detector 12.

An image difference is detected by comparing the brightness distribution between the X-ray image 20 including a phantom region imaged together with a target loaded with an internal load and the selected X-ray reference image 10 (S400).

Figure 8A:
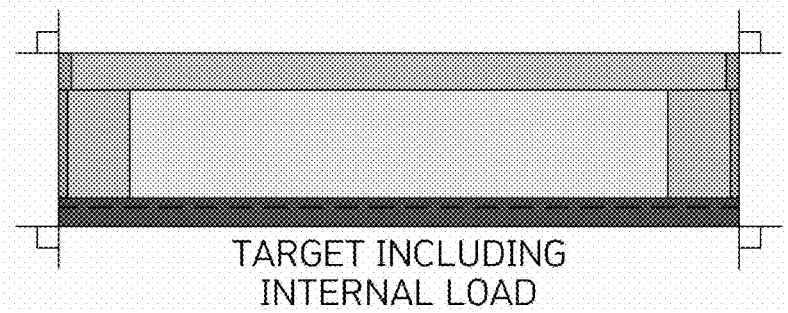
FIGS. 8A, 8B and 8C are a reference diagram for explaining a correction process using a registration phantom in an embodiment of the present disclosure.
Figure 8B:
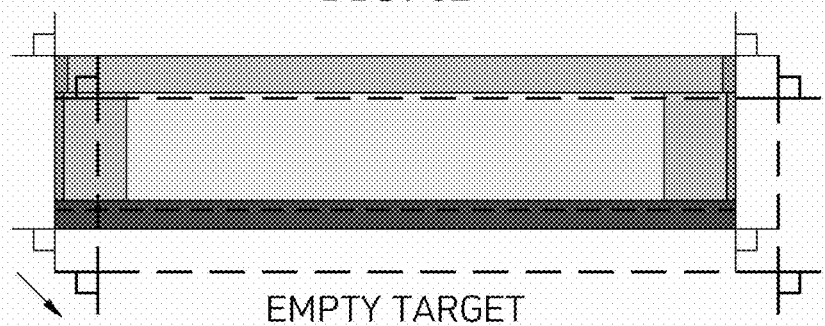
Figure 8C:
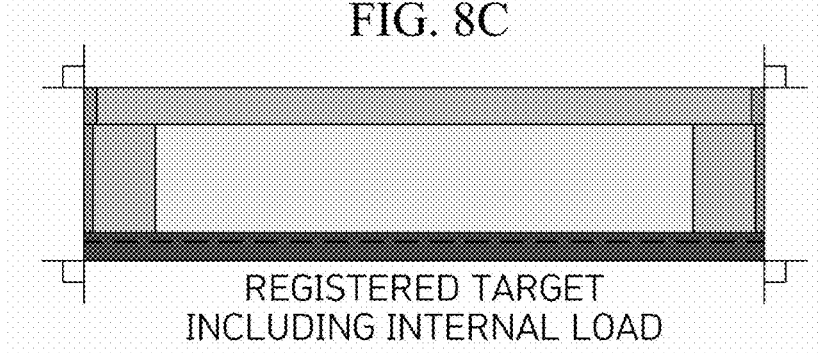

Then, when the difference in the brightness distribution between the X-ray image 20 and the X-ray reference image 10 is detected, calibration and registration are performed using the phantom included in the X-ray image 20 (S500). In this step, when vertices of the target to be imaged by the X-ray imaging unit do not match, a registration phantom installed at each vertex of the target loaded with an internal load is detected as illustrated in FIG. 8A, a position conversion formula is fixed so that the registration phantom has the same position as a registration phantom installed at each vertex of a previously imaged empty target as illustrated in FIG. 8B, and an X-ray image is converted by applying this formula to the X-ray image of the entire target loaded with an internal load as illustrated in FIG. 8C.

Then, the matching unit 500 matches the difference between the X-ray image 20 of the target and the selected X-ray reference image 10, and the load detection unit 600 obtains a difference image from the X-ray image 20 of the matched target and the X-ray reference image 10, and detects an internal load image, from which the background of the X-ray image 20 of the target is removed, through the obtained difference image (S600).

Although the configuration of the present disclosure has been described in detail with reference to the accompanying drawings, this is merely an example, and those skilled in the art to which the present disclosure pertains can make various modifications and changes within the scope of the technical spirit of the present disclosure. Therefore, the scope of protection of the present disclosure should not be limited to the above-described embodiments and should be defined by the description of the appended claims.

Each step included in the method described above may be implemented as a software module, a hardware module, or a combination thereof, which is executed by a computing device.

Also, an element for performing each step may be respectively implemented as first to two operational logics of a processor.

The devices, apparatuses, units, modules, and components described herein with respect to FIGS. 1-8C are implemented by hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods that perform the operations described in this application, and illustrated in FIGS. 1-8C, are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller, e.g., as respective operations of processor implemented methods. One or more processors, or a processor and a controller, may perform a single operation, or two or more operations.

Instructions or software to control computing hardware, for example, one or more processors or computers, to implement the hardware components and perform the methods as described above may be written as computer programs, code segments, instructions or any combination thereof, for individually or collectively instructing or configuring the one or more processors or computers to operate as a machine or special-purpose computer to perform the operations that be performed by the hardware components and the methods as described above. In one example, the instructions or software include machine code that is directly executed by the one or more processors or computers, such as machine code produced by a compiler. In another example, the instructions or software include higher-level code that is executed by the one or more processors or computers using an interpreter. The instructions or software may be written using any programming language based on the block diagrams and the flow charts illustrated in the drawings and the corresponding descriptions in the specification, which disclose algorithms for performing the operations that are performed by the hardware components and the methods as described above.

The instructions or software to control computing hardware, for example, one or more processors or computers, to implement the hardware components and perform the methods as described above, and any associated data, data files, and data structures, may be recorded, stored, or fixed in or on one or more non-transitory computer-readable storage media. Examples of a non-transitory computer-readable storage medium include read-only memory (ROM), random-access programmable read only memory (PROM), EEPROM, RAM, DRAM, SRAM, flash memory, non-volatile memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, blue-ray or optical disk storage, hard disk drive (HDD), solid state drive (SSD), flash memory, a card type memory such as multimedia card micro or a card (for example, secure digital (SD) or extreme digital (XD)), magnetic tapes, floppy disks, magneto-optical data storage devices, optical data storage devices, hard disks, solid-state disks, and any other device that is configured to store the instructions or software and any associated data, data files, and data structures in a non-transitory manner and provide the instructions or software and any associated data, data files, and data structures to one or more processors and computers so that the one or more processors and computers can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent to one of ordinary skill in the art, after an understanding of the disclosure of this application, that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents.

Therefore, the scope of the disclosure is defined not by the detailed description, but by the claims and their equivalents, and all variations within the scope of the claims and their equivalents are to be construed as being included in the disclosure.

What is claimed is:

1. A system for detecting an internal load by using an X-ray image of a container, the system comprising:
an X-ray imaging unit including a source and a director and configured to image a target with X-rays;
a database configured to store an X-ray reference image obtained by imaging a target having an empty interior according to X-ray imaging information including an X-ray imaging condition;
a condition detection unit configured to acquire X-ray imaging information when the target is imaged through the X-ray imaging unit;
a comparison image selection unit configured to select an X-ray reference image corresponding to the acquired X-ray imaging information from the database;
a matching unit configured to match a difference between the X-ray image of the target and the selected X-ray reference image; and
an internal load detection unit configured to obtain a difference image from the X-ray image of the matched target and the X-ray reference image, and to detect an internal loading image having no background of the X-ray image of the target through the obtained difference image.

2. The system of claim 1, wherein the X-ray imaging information includes at least one condition of a standard of an imaging target for a target having an empty interior, a relative geometric condition between the imaging target and the source of the X-rays, a relative geometric condition between the imaging target and the detector, and an X-ray frequency.

3. The system of claim 2, wherein the database stores an X-ray reference image according to the standard of the imaging target for the target having an empty interior, the relative geometric condition between the imaging target and the source of the X-rays, the relative geometric condition between the imaging target and the detector, and the X-ray frequency.

4. The system of claim 1, wherein the database stores at least one X-ray reference image of an X-ray image imaged by a combination of a stationary source and a moving line detector and an X-ray image imaged by a combination of a moving source and the moving line detector.

5. The system of claim 2, wherein in the database, an X-ray reference image, which is imaged using one condition of a distance between the target and the X-ray imaging unit, a height from the ground, an inclination of the target, an X-ray wavelength, a type of the detector of spatial resolution, a calibration phantom, and a type of a registration phantom, is set as a data set for storage.

6. The system of claim 1, wherein the internal load detection unit transmits information on a location and a type of the detected internal load to a display screen.

7. The system of claim 1, further comprising:
a noise removal algorithm for removing grid noise generated between the source and the director during various X-ray imaging.

8. The system of claim 1, further comprising:
a calibration phantom and a registration phantom that are imaged with X-rays together with the target having an internal accommodating space in order to perform calibration and registration of an image taken with X-rays,
wherein the matching unit performs the calibration and the registration by using a predetermined phantom imaged together with the target.

9. The system of claim 8, wherein in the calibration phantom, a sample including a plurality of materials perpendicular to an axis of the source and the detector, which do not overlap each other, and having the same thickness is arranged on a plane parallel to the axis, and
the registration phantom is installed to be able to specify each vertex that does not overlap the internal load of the target.

10. The system of claim 9, wherein the sample is any one of steel and non-ferrous metal.

11. The system of claim 10, wherein the correction unit calibrates and registers the X-ray image of the target loaded with the internal load and the X-ray reference image having the same geometric condition and same wavelength corresponding to the X-ray image.

12. The system of claim 1, wherein the image selection unit detects an X-ray reference image corresponding to the X-ray image from the database, and
detects the X-ray reference image through one of a method of detecting a major key point of a two-dimensional projection container skeleton using a machine learning method including deep learning and a characteristic analysis method, a method of detecting a geometric condition that matches a distribution of a corresponding key point through one-to-one correspondence, and a method of detecting an image imaged with a wavelength that matches or is similar to an X-ray wavelength of the X-ray imaging unit.

13. The system of claim 12, wherein when the X-ray wavelength of the X-ray imaging unit is not matched, the image selection unit detects a phantom for calibration installed so as not to overlap a region of the target loaded with an internal load, fixes a color tone conversion formula through linear or non-linear regression so that two regions have statistically the same brightness distribution, and converts an X-ray image by applying the color tone conversion formula to the X-ray image of the entire target loaded with the internal load, and
when vertices of a target to be imaged by the X-ray imaging unit are not matched, the image selection unit detects a registration phantom installed at each vertex of the target loaded with the internal load, fixes a position conversion formula so that the detected registration phantom have the same position as a registration phantom installed at each vertex of a pre-imaged empty target, and converts an X-ray image by applying the position conversion formula to the X-ray image of the entire target loaded with the internal load.

14. The system of claim 12, wherein the image selection unit performs a comparison using one of a method for comparing a specific geometric condition of the X-ray reference image with geometric conditions corresponding to key points in a one-to-one manner inferred from the X-ray image of the target loaded with the internal load, a method for directly comparing combinations of key points respectively inferred from the X-ray reference image and the X-ray image of the target loaded with the internal load, a method for comparing a specific geometric condition of the X-ray image of the target loaded with the internal load with geometric conditions corresponding to key points in a one-to-one manner inferred from the X-ray reference image, and a method for directly comparing geometric conditions of the X-ray reference image with geometric conditions of the X-ray image of the target loaded with the internal load.

15. The system of claim 12, wherein when geometric conditions, wavelengths, and spatial resolutions of the X-ray image of the target loaded with the internal load and the X-ray reference image do not exactly match, the image selection unit infers and select a new X-ray reference image by a linear or non-linear regression method from X-ray reference images of two or more adjacent conditions according to imaging conditions of the X-ray image of the target loaded with the internal load.

16. The system of claim 1, wherein a difference image between the two X-ray images is obtained by obtaining a log image of the X-ray image of the imaged target, obtaining a difference between the log image of the X-ray image of the target and a log image of the X-ray reference image, and applying an exponential function from the difference.

17. The system of claim 1, wherein when an internal load is detected in an X-ray image of an existing container including no calibration phantom, the image selection unit compares a distribution of shades in a region of a target where no internal load is imaged, that is, a skeletal part constituting a ceiling, a floor, and side walls.

18. The system of claim 1, further comprising:
a learning unit configured to train using a location and a type of the detected internal load.

19. A method for detecting an internal load by using an X-ray image of a container, the method comprising:
a step of, by an X-ray imaging unit including a source and a detector, imaging a target with X-rays;
a step of, by a condition detection unit, acquiring X-ray imaging information when the target is imaged through the X-ray imaging unit;
a step of, by a comparison image selection unit, selecting an X-ray reference image corresponding to the acquired X-ray imaging information from a database;
a step of detecting an image difference by comparing a brightness distribution between an X-ray image including a phantom region imaged together with the target loaded with an internal load and the selected X-ray reference image;
a step of, when the difference in the brightness distribution between the X-ray image and the X-ray reference image is detected, performing calibration and registration using a phantom included in the X-ray image;
a step of, by a matching unit, matches the difference between the X-ray image of the target and the selected X-ray reference image; and
a step of, by a load detection unit, obtaining a difference image from the X-ray image of the matched target and the X-ray reference image, and detecting an internal load image, from which a background of the X-ray image of the target is removed, through the obtained difference image.

20. The method of claim 19, wherein the database includes an X-ray reference image according to a standard of an imaging target for a target having an empty interior, a relative geometric condition between the imaging target and the source of the X-rays, a relative geometric condition between the imaging target and the detector, and an X-ray frequency.

* * * * *